United States Patent [19]

Ogawa et al.

[11] 4,406,894
[45] Sep. 27, 1983

[54] INSECT PESTICIDAL COMPOSITION

[75] Inventors: Haruki Ogawa, Fujieda; Tomonori Shimazu, Shizuoka, both of Japan

[73] Assignees: Kumiai Chemical Industry Co., Ltd., Tokyo; Kuraray Co., Ltd., Kurashiki, both of Japan

[21] Appl. No.: 306,671

[22] Filed: Sep. 29, 1981

[30] Foreign Application Priority Data

Sep. 30, 1980 [JP] Japan ............................... 55/136005

[51] Int. Cl.³ ...................... A01N 37/08; A01N 57/00
[52] U.S. Cl. ..................................... 424/225; 424/305
[58] Field of Search ................................ 424/225, 305

[56] References Cited

U.S. PATENT DOCUMENTS 3,156,718  11/1964  Lorenz et al. ........................ 260/970
3,973,036  8/1976  Hirano et al. ........................ 424/304

FOREIGN PATENT DOCUMENTS 223447  8/1981  Argentina .
2757768  6/1978  Fed. Rep. of Germany .
46-2038  1/1971  Japan .
54-147927  11/1979  Japan .
2048255  12/1980  United Kingdom .

*Primary Examiner*—Allen J. Robinson
*Attorney, Agent, or Firm*—Oblon, Fisher, Spivak, McClelland & Maier

[57] ABSTRACT

An insect pesticidal composition comprises O,O-di-$C_{2-3}$ alkyl S-benzyl- or S-halobenzyl-phosphorothiolate and a pyrethroid compound having the formula

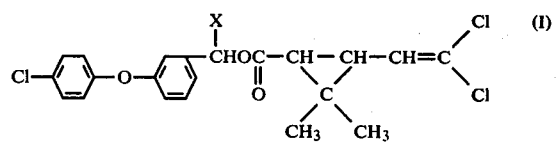

wherein X represents hydrogen atom or ethynyl group as active ingredients.

8 Claims, No Drawings

INSECT PESTICIDAL COMPOSITION

BACKGROUND OF THE INVENTION

1. Field of the Invention:

The present invention relates to an insect pesticidal composition. More particularly, it relates to an insect pesticidal composition which controls pests for rice such as brown planthopper and sanitary pests at a small dose.

2. Description of Prior Arts:

As virus diseases on rice plants in Japan and South East Asia, dwarf, stripe, black-streaked dwarf and yellow dwarf, being medicated by green rice leafhopper and smaller brown planthopper, have been known and necrotic mosaic caused by a soil infection has been known.

Recently, breeding of grassy stunt has been found in Kyushu District of Japan and the breeding of grassy stunt has been especially severe in South west of Kyushu District though the breeding of grassy stunt has been found in only South East Asia. The diseased rice plants causes deterioration of quality of rice. The grassy stunt is serious disease in the torrid zone. The mediation of the virus is made by brown planthoppers which come from Southern zone to Japan in rainy season and seriously breed on rice in paddy field. The breeding of grassy stunt in Western District of Japan, especially Kyushu District, indicates the effect of disease in the Southern zone to Japan. The enlargement of the breeding of grassy stunt is anxiously considered. It is important to control brown planthopper in the zone for the breeding of the virus, as soon as possible.

Brown planthopper widely inhabits in paddy fields in Asia and come from such zone to Japan with South Western wet worm wind in rainy season. It is impossible to prevent invasion of the imago of brown planthopper. Therefore, it is difficult to prevent initial infection. In the South west of Kyushu District, it is important to reduce the initial infection. Moreover, it is necessary to effectively prevent secondary infection. It is necessary to control brown planthopper by pesticide. However, there are various problems because of lowering of sensitivity to insect pesticides.

The pyrethroid compounds used in the present invention have the formula

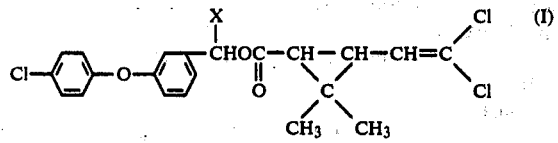

wherein X represents hydrogen atom or ethynyl group. The pyrethroid compound (I) having ethynyl group as X is known as an insect pesticide which is effective to agricultural pests such as rice stem borer, smaller brown planthopper (Laodelphax striatellus), green rice leafhopper (Nephotettix cincticeps) (refer to Japanese Unexamined Patent Publication No. 33452/1980). The pyrethroid compound (I) having hydrogen atom as X is a novel compound which has insect pesticidal effect to green rice leafhopper (Nephotettix cincticeps), rice stem borer, tobacco cutworm, smaller brown planthopper (Laodelphax striatellus), etc. However, the pesticidal effect of these pyrethroid compound (I) to brown planthopper is not satisfactory. When the pyrethroid compound (I) is applied, the effect is not always stable.

In the practical application, it is preferable to combine it with a synergistic active ingredient.

On the other hand, O,O-di-C$_{2-3}$ alkyl S-benzyl- or S-halobenzyl-phosphorothiolates, especially O,O-diisopropyl S-benzylphosphorothiolate or O,O-diisopropyl S-halobenzyl-phosphorothiolate (hereinafter referred to as IBP) has excellent germicidal effect on agricultural germs for rice etc., however, does not have effective insect pesticidal effect on agricultural insect pests at a practical dose.

SUMMARY OF THE INVENTION

It is an object of the present invention to provide an insect pesticidal composition which maintains advantages of the pyrethroid compound (I) but overcomes disadvantages of the pyrethroid compound (I).

It is another object of the present invention to provide an insect pesticidal composition which control insect pests of Hemiptera, Lepidoptera or Diptera, especially brown planthopper.

It is the other object of the present invention to provide an insect pesticidal composition which displays excellent synergistic effect and has low toxicity to be safely applied.

The foregoing and other objects of the present invention have been attained by providing an agricultural insect pesticidal composition which comprises O,O-di-C$_{2-3}$ alkyl S-benzyl- or S-halobenzyl-phosphorothiolate and a pyrethroid compound having the formula

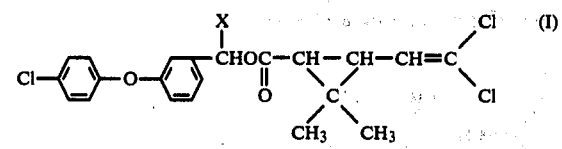

wherein X represents hydrogen atom or ethynyl group as active ingredients.

DETAILED DESCRIPTION OF THE PREFERRED EMBODIMENTS

The insect pesticidal composition of the present invention comprises the pyrethroid compound having the formula (I) and O,O-di-C$_{2-3}$ alkyl S-benzyl- or S-halobenzyl-phosphorothiolate such as O,O-diisopropyl- or O,O-diethyl-S-benzyl- or S-halobenzyl-phosphorothiolate.

The composition can be only a mixture of the active ingredients which will be applied after diluting them. The active ingredients can be mixed with desired adjuvants such as carriers, diluents, surfactants and dispersing agents at a desired rate to obtain applicable formulations such as dust, wettable powder, flowable, micro granule, granule, oil preparation, aerosol, vaporizable and emulsifiable concentrate. These formulations may be applied directly or after being diluted at a proper concentration. The active ingredients each can be separately formulated to mix them at the time for application.

Suitable carriers include solid carriers such as talc, bentonite, clay, kaolin, diatomaceous earth, fine silica, vermiculite, calcium hydroxide, silicate, ammonium sulfate and urea; and liquid carriers such as isopropyl alcohol, xylene, cyclohexanone and kerosene.

Suitable surfactants and dispersing agents include alkyl sulfates, alkylsulfonates, ligninsulfonates, polyoxyethyleneglycol ethers, polyoxyethylenealkylaryl ethers and polyoxyethylenesorbitane monoalkylates.

The other adjuvants include carboxymethyl cellulose, polyoxyethyleneglycol and gum arabic.

The concentration of the active ingredients in the application is not critical and usually in a range of 5 to 5,000 ppm preferably 20 to 2,000 ppm. When the active ingredients are applied in paddy field, the concentration can be lower. A dose of the active ingredient is usually in a range of 0.001 to 1 kg/10 are preferably 0.01 to 0.5 kg/10 are.

O,O-di-$C_{2-3}$ alkyl S-benzyl- or S-halobenzyl-phosphorothiolates have the formula

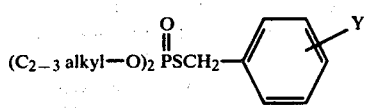
(II)

(Y is hydrogen or halogen atom).

The typical compounds have the formula (II) wherein Y is hydrogen or chlorine atom and the $C_{2-3}$ alkyl group is isopropyl or ethyl group.

O,O-diisopropyl S-benzyl- or S-chlorobenzyl-phosphorothiolates are referred to as IBP (1) and (2).

IBP (1): O,O-diisopropyl S-benzyl-phosphorothiolate:

IBP (2): O,O-diisopropyl S-3-chlorobenzyl-phosphorothiolate:

The pyrethroid compounds (I) are as follows. A mixture of them can be also used.

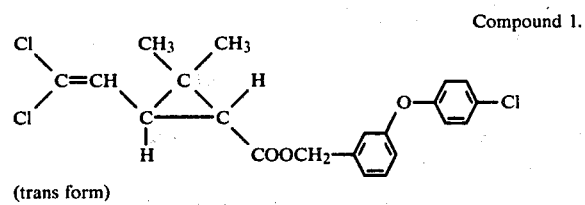
Compound 1.
(trans form)

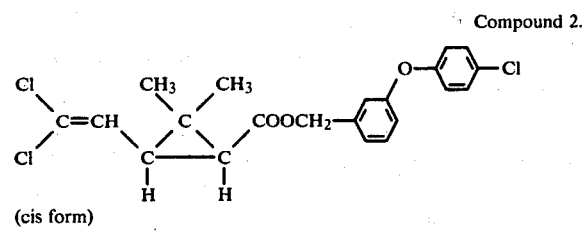
Compound 2.
(cis form)

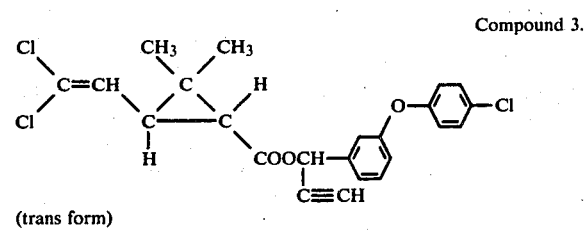
Compound 3.
(trans form)

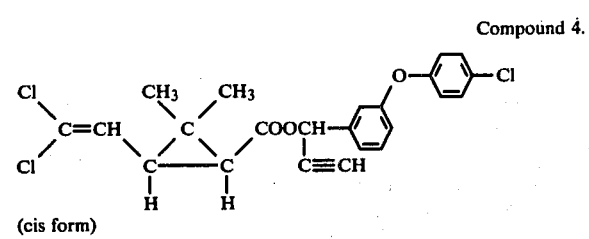
Compound 4.
(cis form)

These compounds can be produced by the below-mentioned process as Reference.

A ratio of the pyrethroid compound (I) to IBP is in a range of 1:10 to 10:1 preferably 2:1 to 1:10 especially 1:3 to 1:10.

Unlike the conventional chrysanthemummonocarboxylates, the pyrethroid compound (I) are highly stable against light, heat or oxidation. However, if it is considered necessary, for example when exposure to a highly oxidative environment is expected, an insect pesticidal composition with stabilized efficacy can be prepared by incorporating suitable amounts of an antioxidant or an ultraviolet absorbent, for example, phenol derivatives such as BHT (2,6-di-tert-butyl-4-methyl phenol) and BHA (butyl hydroxy anisole); bisphenol derivatives and arylamines such as phenyl α-naphthylamine, phenyl β-naphthylamine and condensate of phenetidine and acetone; and benzophenone compounds as stabilizers.

It is also possible to incorporate the other active ingredient such as other insect pesticides, germicides and miticides to obtain agricultural compositions having further effects.

The insect pesticidal composition of the present invention is a combination of the pyrethroid compound and IBP to display unexpected synergistic insect pesticidal effect to brown planthopper etc. which can not be expected by the use of a single compounds.

The insect pesticidal compositions of the present invention have immediate effect, high lethal effect and residual effect for controlling the following insect pests other than brown planthopper (*Nilaparvata lugens*): Rice insect pests for rice plant such as rice stem borer (*Chilo suppressalis*), green rice leafhopper (*Nephotettix cincticeps*), planthoppers, bugs, rice leaf beetle (*Oulema oryzae*), rice leaf miner (*Agromyza oryzae*), grass leafroller (*Cnaphalocrocis medinalis*), rice plant skipper (*Parnara guttata*), rice water weevil (*Lissorhoptrus oryzophilus*) and weevils; insect pest for farmland plant such as tobacco cutworm (*Spodoptera litura*), diamond back moth (*Plutella xylostella*), cabbage worms, aphids, cutworms; insect pest for fruit trees such as tortrixes, mites and fruit moths; insect pest for forest such as fall webworm (*Hyphantria cunea*), gypsy moth (*Lymantria dispar*) and beetles; stored grain insect pest such as rice weevils and indian meal moth (*Plodia interpunctella*); and sanitary insect pest such as houseflies, mosquitoes and cockroaches.

The insect pesticidal compositions can be prepared as follows:

Dust:

Active ingredient: 0.1 to 10 wt.% preferably 0.5 to 5 wt.%

Solid carrier: 99.9 to 90 wt.% preferably 99.5 to 95 wt.%

The active ingredients are mixed with fine solid carrier and the mixture is pulverized.

Emulsifiable concentrate:

Active ingredient: 5 to 90 wt.% preferably 20 to 70 wt.%

Surfactant: 1 to 40 wt.% preferably 5 to 20 wt.%

Liquid carrier: 9 to 94 wt.% preferably 10 to 75 wt.%.

The active ingredients are dissolved in the liquid carrier and the surfactant is admixed.

Wettable powder:

Active ingredient: 5 to 90 wt.% preferably 10 to 50 wt.%

Surfactant: 1 to 20 wt.% preferably 5 to 10 wt.%
Solid carrier: 9 to 94 wt.% preferably 40 to 85 wt.%.

The active ingredients are admixed with the solid carrier and the surfactant and the mixture is pulverized.

Oil preparation:

Active ingredient: 0.05 to 50 wt.% preferably 0.1 to 30 wt.%

Liquid carrier: 99.95 to 50 wt.% preferably 99.9 to 70 wt.%

The active ingredients are dissolved in the liquid carrier.

Aerosol preparation:

Active ingredient: 0.1 to 10 wt.% preferably 0.5 to 5 wt.%

Liquid carrier: 99.9 to 90 wt.% preferably 99.5 to 95 wt.%.

The active ingredients are mixed with the liquid carrier and the mixture is charged in an aerosol container and a valve is fitted and a propellant is compressed through the valve to obtain an aerosol preparation.

The production of the pyrethroid compound used in the present invention, the preparations and effects of the insect pesticidal compositions are illustrated by References, Preparations and Experiments.

REFERENCE 1

(Production of Compound 2)

In 20 ml. of dry benzene, 2.28 g. of cis-2,2-dimethyl 3-(2,2-dichlorovinyl)cyclopropanecarbonyl chloride was dissolved and then, 2.34 g. of 3-(4-chlorophenoxy)-benzyl alcohol and 1.58 g. of pyridine were added to the solution and the mixture was stirred at room temperature overnight. The reaction mixture was washed with a dilute hydrochloric acid and with water and then dried over anhydrous magnesium sulfate and low boiling fraction was distilled off under a reduced pressure to obtain an oily product.

The product was purified by a preparative liquid chromatography (Prep LC/System 500, Prep PAK-500(trade name)/Silica Column manufactured by Waters Associates, mixed solvent of diisopropyl ether/n-hexane=6:94 vol. ratio) to obtain 3.91 g. of 3-(4-chlorophenoxy) benzyl cis-2,2-dimethyl-3-(2,2-dichlorovinyl)-cyclopropanecarboxylate (Compound 2) having the following NMR spectrum (yield: 92%). NMR spectrum (90 MHz)

$\delta_{HMS}{}^{CDCl_3}$: 1.17(s) 6H, 1.72–2.08 (m) 2H, 5.00 (s) 2H, 6.18 (d) 1H, 6.80–7.38 (m) 8H.

REFERENCE 2

(Production of Compound 1)

In accordance with the process of Reference 1 except using trans-2,2-dimethyl-3-(2,2-dichlorovinyl)cyclopropanecarbonyl chloride instead of cis-2,2-dimethyl-3-(2,2-dichlorovinyl)cyclopropanecarbonyl acid chloride, 3.81 g. of 3-(4-chlorophenoxy)benzyl trans-2,2-dimethyl-3-(2,2-dichlorovinyl)cyclopropanecarboxylate (Compound 1) having the following NMR spectrum was obtained (yield: 90%). NMR spectrum (90 MHz)

$\delta_{HMS}{}^{CDCl_3}$: 1.11 (s) 3H, 1.21 (s) 3H, 1.56 (d) 1H, 2.18 (dd) 1H, 5.03 (s) 2H, 5.53 (d) 1H, 6.80–7.38 (m) 8H.

REFERENCE 3

(Production of Compound 3 and Compound 4)

In 120 ml. of dry benzene was dissolved 11.4 g. of 2,2-dimethyl-3-(2,2-dichlorovinyl)cyclopropanecarbonyl chloride (cis-/trans-ratio=50:50, approx.) followed by addition of 12.9 g. of 3-(4-chlorophenoxy)-α-ethynylbenzyl alcohol and further by dropwise addition of 7.9 g. of pyridine. The mixture was stirred at room temperature overnight. Thereafter, the reaction mixture was diluted with 100 g. for water and the benzene layer was separated, washed with dilute hydrochloric acid and water and dried over anhydrous magnesium sulfate. The low-boiling fraction was then distilled off under reduced pressure to recover an oil. This oily product was purified by preparative liquid chromatography (Prep LC/System 500, Prep PAK trade name 500/Silica Column manufactured by Waters Associates, mixed solvent of diethyl ether/n-hexane=2:98 vol. ratio). The above procedure yielded 20.2 g. of 3-(4-chlorophenoxy)-α-ethynylbenzyl 2,2-dimethyl-3-(2,2-dichlorovinyl) cyclopropanecarboxylate (yield: 90%). The separation of cis- and trans-isomers from each other can be effected by the above-mentioned preparative liquid chromatography. The NMR spectra of such isomers are indicated below.

NMR spectra (90 MHz) $\delta_{HMS}{}^{CDCl_3}$

| trans-Isomer: (Compound 3) | 1.08, 1.13, 1.17, 1.25(each s)6H; |
|---|---|
|  | 1.56(d), 1.58(d)1H; |
|  | 2.04–2.31(m)1H; |
|  | 2.52–2.61(m)1H; |
|  | 5.55(d)1H; |
|  | 6.36–6.43(m)1H; |
|  | 6.76–7.43(m)8H |
| cis-Isomer: (Compound 4) | 1.13, 1.16, 1.20, 1.23(each s)6H; |
|  | 1.72–2.10(m)2H; |
|  | 2.53–2.60(m)1H; |
|  | 6.16(d), 6.18(d)1H; |
|  | 6.32–6.40(m)1H; |
|  | 6.75–7.43(m)8H |

Preparation 1: (Dust)

A mixture of 0.5 wt.part of Compound 1 and 3 wt.parts of IBP (1) was dissolved in 20 wt.parts of acetone, followed by addition of 96.5 wt. parts of talc (300 mesh). After thorough stirring, the acetone was distilled off to obtain a dust of the present invention.

Preparation 2: (Emulsifiable concentrate)

A uniform emulsifiable concentrate of the present invention was obtained by sequentially mixing 3 wt.parts of Compound 2, 30 wt. parts of IBP (1), 53 wt.parts of xylene and 14 wt.parts of nonionic surfactant (Sorpol: manufactured by Toho Kagaku Kogyo K.K.) and thoroughly stirring the resulting mixture.

Preparation 3: (Wettable powder)

A wettable powder of the present invention was obtained by mixing 20 wt. parts of Compound 3 with 20 wt. parts of IBP (1), adding 5 wt. parts of nonionic surfactant (Sorpol) and 55 wt. parts of fine silica (silica hydrate) to the resulting mixture and thoroughly mixing and milling them in a mill.

Preparation 4: (Oil preparation)

An oil preparation of the present invention was obtained by mixing 0.05 wt. part of Compound 1 with 0.05 wt. part of IBP (1) and dissolving the mixture in kerosene to be 100 wt. parts.

Preparation 5: (Aerosol preparation)

A solution of 0.2 wt. part of Compound 2 and 2.0 wt. parts of IBP (1) in 5 wt. parts of xylene and 7.8 wt. parts of kerosene was charged in an aerosol container. After a valve was mounted to the container, the aerosol dispenser was pressurized by charging 85 wt. parts of propellant (liquefied petroleum gas) to obtain an aerosol preparation.

Preparation 6: (Dust)

0.3 Wt. part of Compound 1, 2, 3 or 4, 1 wt. part of IBP (1) or (2), 1.2 wt. parts of fine silica and 97.5 wt. parts of clay were mixed and pulverized to obtain each dust of the present invention.

Preparation 7: (Dust)

0.8 Wt. part of Compound 1, 2, 3 or 4, 4 wt. parts of IBP (1) or (2), 3.2 wt. parts of fine silica and 92 wt. parts of clay were mixed and pulverized to obtain each dust of the present invention.

Preparation 8: (Emulsifiable concentrate)

Each uniform emulsifiable concentrate of the present invention was obtained by sequentially mixing 3 wt. parts of Compound 1, 2, 3 or 4, 18 wt. parts of IBP (1) or (2), 64 wt. parts of xylene and 15 wt. parts of nonionic surfactant (Sorpol SNX) and thoroughly stirring the resulting mixture.

Preparation 9: (Emulsifiable concentrate)

Each uniform emulsifiable concentrate of the present invention was obtained by sequentially mixing 30 wt. parts of Compound 1, 2, 3 or 4, 30 wt. parts of IBP (1) or (2), 25 wt. parts of xylene and 15 wt. parts of nonionic surfactant (Sorpol SNX) and thoroughly stirring the resulting mixture.

Preparation 10: (Wettable powder)

Each wettable powder of the present inventiomn was obtained by mixing 10 wt. parts of Compound 1, 2, 3 or 4, 15 wt. parts of IBP (1) or (2), 3 wt. parts of sodium alkylbenzenesulfonate, 3 wt. parts of polyvinyl alcohol, 40 wt. parts of fine silica and 29 wt. parts of diatomaceous earth and uniformly pulverizing the resulting mixture.

Preparation 11: (Oil preparation)

Each oil preparation of the present invention was obtained by dissolving 10 wt. parts of Compound 1, 2, 3 or 4 and 10 wt. parts of IBP (1) or (2) in 80 wt. parts of xylene.

Test Experiment 1: (Mortality test with brown planthopper)

A pot having a diameter of 10 cm with two rice seedings at 5 leaf stage was covered with a wire-mesh cage and the female adults of brown planthopper were released therein.

Each dust was sprayed on the test insects by bell-jar dusting chamber having a bottom area of 500 cm² under a reduced pressure of 20 cmHg at each dose. The pot was kept in said chamber for 2 minutes. Bell-jar dusting chamber was taken out and each pot was kept in a green-house. After 24 hours, the test insects were examined for deaths and the percent mortality was measured. The result are shown in Table 1.

TABLE 1

| Active ingredient | Dose (mg/bell-jar) | Amount of active ingredient (mg/bell-jar) | Number of insects | Percent mortality (%) |
|---|---|---|---|---|
| Compound 1 | 0.5% | 12.5 | 0.0625 + 0.375 | 30 | 60.0 |
| IBP (1) | 3% | 25 | 0.125 + 0.75 | 30 | 93.3 |
| | | 50 | 0.25 + 1.5 | 30 | 100 |
| Compound 2 | 0.5% | 12.5 | 0.0625 + 0.375 | 30 | 43.3 |
| IBP (1) | 3% | 25 | 0.125 + 0.75 | 30 | 90.0 |
| | | 50 | 0.25 + 1.5 | 30 | 100 |
| Compound 3 | 0.5% | 12.5 | 0.0625 + 0.375 | 30 | 70.0 |
| IBP (1) | 3% | 25 | 0.125 + 0.75 | 30 | 93.3 |
| | | 50 | 0.25 + 1.5 | 30 | 96.7 |
| Compound 1 | 0.5% | 12.5 | 0.0625 | 30 | 6.7 |

TABLE 1-continued

| Active ingredient | Dose (mg/bell-jar) | Amount of active ingredient (mg/bell-jar) | Number of insects | Percent mortality (%) |
|---|---|---|---|---|
| | | 25 | 0.125 | 30 | 6.7 |
| | | 50 | 0.25 | 30 | 60.0 |
| Compound 2 | 0.5% | 12.5 | 0.0625 | 30 | 0 |
| | | 25 | 0.125 | 30 | 23.3 |
| | | 50 | 0.25 | 30 | 80.0 |
| Compound 3 | 0.5% | 12.5 | 0.0625 | 30 | 6.7 |
| | | 25 | 0.125 | 31 | 54.8 |
| | | 50 | 0.25 | 29 | 92.9 |
| IBP (1) | 3% | 50 | 1.5 | 30 | 3.3 |
| | | 100 | 3 | 30 | 13.8 |
| S-2539 | 0.8% | 12.5 | 0.1 + 0.375 | 30 | 6.7 |
| IBP (1) | 3% | 25 | 0.2 + 0.75 | 30 | 76.7 |
| | | 50 | 0.4 + 1.5 | 30 | 100 |
| Non-treatment | — | | | 30 | 0 |

Note:
50 mg/bell-jar corresponds to a dose of 1 kg/10 ares.

Text Experiment 2:

(Mortality with larvae of resistant green rice leafhopper at various temperatures)

Three seedlings at 3 leaf stage were put in an ink bottle, their stems being fixed with a rubber stopper. Each dust was sprayed on the seedlings by bell-jar dusting chamber having a bottom area of 1,300 cm² under a pressure of 560 mmHg. The bottle was kept in said chamber for 2 minutes. After spraying the dust, the bottle was environed with a glass cylinder and the cylinder was covered with an aluminum cap. Each bottle was kept in each constant temperature chamber at 15° C., 23° C. or 30° C. and larvae of resistant green rice leafhopper were released into the cylinder. After 24 hours, the test insects were examined for deaths and the percent mortality was measured. The results are shown in Table 2.

TABLE 2

| Active ingredient | Amount of active ingredient (%) | Dose (mg/bell-jar) | Temperature percent mortality (%) | | |
|---|---|---|---|---|---|
| | | | 15° C. | 23° C. | 30° C. |
| Compound 1 + IBP (1) | 0.5 + 3.0 | 65 | 100 | 96.6 | 70.0 |
| Compound 2 + IBP (1) | 0.5 + 3.0 | 65 | 93.5 | 96.7 | 53.3 |
| Compound 1 | 0.5 | 65 | 96.7 | 78.1 | 63.3 |
| Compound 2 | 0.5 | 65 | 63.3 | 40.0 | 6.7 |
| IBP (1) | 5.0 | 65 | 0 | 0 | 0 |
| Non-treatment | — | — | 0 | 0 | 0 |

Test Experiment 3:

(Mortality test with brown planthopper in variation of ratio of Compound 1 to IBP)

Each rice seedling at 3 leaf stage was dipped in each solution of predetermined concentrations of active ingredients, dried in air and put in an ink bottle filled with water. The bottle was environed with a glass cylinder and female adults of brown planthopper were released therein and the cylinder was covered with an aluminum cap. Each bottle was kept in a constant temperature chamber at 25° C. After 24 hours, the test insects were examined for deaths and the percent mortality was measured. The results are shown in Table 3.

TABLE 3

| Concentration (ppm) IBP (1) | Concentration (ppm) Comp. 1 | Ratio of active ingredient IBP (1):Comp. 1 | Number of insects | Percent mortality (%) |
|---|---|---|---|---|
| 1000 | 0 | 10:0 | 30 | 20.0 |
| 900 | 100 | 9:1 | 30 | 80.0 |
| 800 | 200 | 8:2 | 30 | 90.0 |
| 700 | 300 | 7:3 | 30 | 93.3 |
| 600 | 400 | 6:4 | 30 | 93.3 |
| 500 | 500 | 5:5 | 30 | 100 |
| 400 | 600 | 4:6 | 30 | 100 |
| 300 | 700 | 3:7 | 30 | 96.7 |
| 200 | 800 | 2:8 | 30 | 93.3 |
| 100 | 900 | 1:9 | 30 | 83.3 |
| 0 | 1000 | 0:10 | 30 | 53.3 |
| Non-treatment | | — | 30 | 0 |

Test Experiment 4:
(Mortality test with brown planthopper)

A pot having a square section of 10 cm × 10 cm with 5 rice seedlings at 6 leaf stage was prepared. Each dust was sprayed on the seedlings by bell-jar dusting chamber having a bottom area of 1300 cm² under a reduced pressure of 20 cmHg at each dose. The pot was kept in said chamber for 2 minutes. After spraying, the pot was covered with a cylindrical wire-mesh cage and female adults of brown planthopper were released therein. After 24 hours, the test insects were examined for deaths and the percent mortality was measured. The results were repeated for three times by using ten test insects in each test in a greenhouse. The results are shown in Table 4.

TABLE 4

| Active ingredient | Amount of active ingredient (%) | Dose (mg/bell-jar) | Percent mortality (%) |
|---|---|---|---|
| Comp. 1 | 0.3 | 390 | 6.7 |
| (60:40) | | 130 | 3.3 |
| Comp. 2 | 0.5 | 390 | 33.3 |
| | | 130 | 3.3 |
| | 0.8 | 390 | 55.2 |
| | | 130 | 3.3 |
| IBP(1) | | | |
| Comp. 1 | 0.3    3 | 390 | 100 |
| (60:40) | | 130 | 66.7 |
| Comp. 2 | 0.5    3 | 390 | 100 |
| | | 130 | 96.7 |
| IBP (1) | 0.8    3 | 390 | 100 |
| | | 130 | 100 |
| IBP (1) | 3 | 390 | 6.7 |
| | | 130 | 0 |
| Non-treatment | — — | 0 | 0 |

Note:
130 mg/bell-jar corresponds to a dose of 1 kg/10 ares.

Test Experiment 5:
(Mortality test with larvae of resistant diamond back moth)

Each Chinese kale leaf was dipped in each solution of predetermined concentrations of active ingredients for 1 minute, dried in air and put in each plastic cup having a diameter of 5.5 cm and a height of 4 cm and larvae of resistant diamond back moth were released therein. Each cup was kept in a constant temperature chamber at 25° C. After 48 hours, the test insects were examined for deaths and the percent mortality was measured. The test was repeated for three times by using 10 test insects in each test. The results are shown in Table 5.

TABLE 5

| Active ingredient | Concentration (ppm) | Percent mortality (%) |
|---|---|---|
| Compound 1 | 200 | 30.0 |
| | 40 | 6.7 |
| Compound 2 | 200 | 50.0 |
| | 40 | 26.7 |
| Compound 1 | 200 + 200 | 90.0 |
| IBP (1) | 40 + 40 | 70.0 |
| Compound 2 | 200 + 200 | 100 |
| IBP (1) | 40 + 40 | 76.7 |
| IBP (1) | 200 | 6.7 |
| Non-treatment | — | 0 |

Test Experiment 6:
(Mortality with larvae of green rice leafhopper)

Five seedlings at 3 leaf stage were dipped in a solution of an active ingredient at a predetermined concentration and dried in air and were put in an ink bottle by fixing the stem with a rubber stopper. The bottle was environed with a glass cylinder and 10 larvae of green rice leafhopper were released into the cylinder and the cylinder was covered with an aluminum cap. Each bottle was kept in a constant temperature chamber at 25° C. After 24 hours, the test larvae were examined for deaths and each percent mortality was measured.

A co-toxicity coefficient of each composition of two active ingredients was calculated by the method of Sun and Johson (1960)

$$\text{Co-toxicity coefficient} = \frac{LC_{50} \text{ of main active ingredient}}{LC_{50} \text{ of main active ingredient with additive}}$$

(Non-toxicity of additive) The results are shown in Table 6.

TABLE 6

| Active ingredient | $LC_{50}$ (ppm) | Co-toxicity coefficient |
|---|---|---|
| Compounds 3 and 4 (1:1) | 23 | |
| IBP (2) | >8,000 | |
| Compounds 3 and 4 (1:1) + IBP (2) (1:1) | 9 | 5.1 |

The same results were found when O,O-diisopropyl S-4-chlorobenzyl-phosphorothiolate, O,O-diethyl S-benzyl-phosphorothiolate or O,O-diethyl S-3-chlorobenzyl-phosphorothiolate was used in accordance with Test Experiment 6 instead of IBP (2).

We claim:

1. An insect pesticidal composition which comprises O,O-di-$C_{2-3}$ alkyl S-benzyl- or S-halobenzyl-phosphorothiolate and a pyrethroid compound having the formula

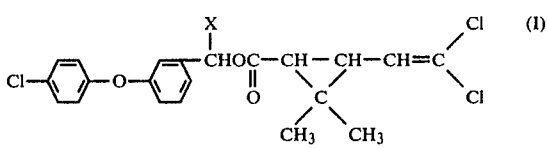

wherein X represents hydrogen atom or ethynyl group as active ingredients and wherein the ratio of the pyrethroid compound to the phosphorothiolate compound is in the range of 1:10 to 10:1.

2. The insect pesticidal composition according to claim 1 wherein a ratio of the pyrethroid compound to the O,O-di-$C_{2-3}$ alkyl S-benzyl- or S-halobenzyl-phosphorothiolate is in a range of 2:1 to 1:10.

3. The insect pesticidal composition according to claim 1 wherein the O,O-di-$C_{2-3}$ alkyl S-benzyl- or S-halobenzyl-phosphorothiolate is O,O-diisopropyl S-benzyl-phosphorothiolate, O,O-diisopropyl S-halobenzyl-phosphorothiolate, O,O-diethyl S-benzyl-phosphorothiolate or O,O-diethyl S-halobenzyl-phosphorothiolate.

4. The insect pesticidal composition according to claim 1 wherein the O,O-di-$C_{2-3}$ alkyl S-benzyl-phosphorothiolate is O,O-diisopropyl S-benzylphosphorothiolate.

5. The insect pesticidal composition according to claim 1 wherein an effective amount of an antioxidant or an ultraviolet absorber is incorporated.

6. The insect pesticidal composition according to claim 1 wherein a carrier and a surfactant are incorporated as a diluent and a dispersing agent or an emulsifier.

7. The insect pesticidal composition according to claim 1 which comprises an inert carrier.

8. The insect pesticidal composition according to claim 1 which comprises a total of said active ingredients in a range of 0.05 to 90% by weight.

* * * * *